United States Patent
Yu et al.

(10) Patent No.: US 9,583,650 B1
(45) Date of Patent: Feb. 28, 2017

(54) INTEGRATED PLASMONIC CIRCUIT AND METHOD OF MANUFACTURING THE SAME

(71) Applicant: KOREA ADVANCED INSTITUTE OF SCIENCE AND TECHNOLOGY, Daejeon (KR)

(72) Inventors: Kyoungsik Yu, Daejeon (KR); Kyungmok Kwon, Daejeon (KR); Kyunghan Choi, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/052,305

(22) Filed: Feb. 24, 2016

(30) Foreign Application Priority Data

Jan. 15, 2016 (KR) .................. 10-2016-0005556

(51) Int. Cl.
*H01L 29/00* (2006.01)
*H01L 31/0232* (2014.01)
(Continued)

(52) U.S. Cl.
CPC .......... *H01L 31/0232* (2013.01); *B82Y 10/00* (2013.01); *G01N 21/554* (2013.01);
(Continued)

(58) Field of Classification Search
CPC ...... B82Y 10/00; G02B 6/1226; G02B 5/008; G02F 2203/10; G01N 21/554; H01L 49/006
See application file for complete search history.

(56) References Cited

U.S. PATENT DOCUMENTS

| | | | |
|---|---|---|---|
| 2010/0126566 A1* | 5/2010 | Ji | G02B 5/008 136/252 |
| 2011/0156000 A1* | 6/2011 | Cheng | H01L 33/22 257/13 |

(Continued)

FOREIGN PATENT DOCUMENTS

| | | |
|---|---|---|
| KR | 101559194 B1 | 10/2015 |
| KR | 1020150138890 A | 12/2015 |

OTHER PUBLICATIONS

Kwon, K. et al., "Electrically Driven Surface Plasmon Polaritons Circuits," Japan Society of Applied Physics, 20th Microoptics Conference (MOC '15), Fukuoka, Japan, Oct. 25, 2015, 2 pages.

*Primary Examiner* — Ngan Ngo
(74) *Attorney, Agent, or Firm* — John D. Russell

(57) ABSTRACT

Provided are a integrated plasmonic circuit including a plasmonic source using a surface plasmon resonance phenomenon, a plasmonic detector detecting an optical signal generated in the plasmonic source, and a link structure between the plasmonic source and the plasmonic detector, that is, a signal transferring part, and a method of manufacturing the same. Provided are a integrated plasmonic circuit capable of realizing both of miniaturization and speed improvement by overcoming both of a limitation of an electronic device in terms of a signal speed in spite of being excellent in terms of miniaturization efficiency and a limitation of an existing optical device in terms of miniaturization due to a diffraction limitation of light in spite of being improved in terms of a signal speed, and a method of manufacturing the same.

7 Claims, 8 Drawing Sheets

(51) Int. Cl.
  *G02B 6/122*  (2006.01)
  *G01N 21/65*  (2006.01)
  *B82Y 10/00*  (2011.01)
  *H01L 49/00*  (2006.01)
  *G02B 5/00*  (2006.01)
  *G01N 21/552*  (2014.01)
(52) U.S. Cl.
  CPC ........... *G01N 21/658* (2013.01); *G02B 5/008* (2013.01); *G02B 6/1226* (2013.01); *H01L 49/00* (2013.01); *G02F 2203/10* (2013.01)

(56) References Cited

U.S. PATENT DOCUMENTS

| | | | | |
|---|---|---|---|---|
| 2013/0115413 | A1* | 5/2013 | Eres | G01N 21/01 428/120 |
| 2013/0155484 | A1* | 6/2013 | Sweatlock | G02F 1/23 359/282 |
| 2014/0010509 | A1* | 1/2014 | Zayets | G02B 6/10 385/131 |
| 2015/0063748 | A1* | 3/2015 | Zhang | G02B 6/1226 385/28 |
| 2016/0024639 | A1* | 1/2016 | Cheah | C23C 14/081 216/95 |

* cited by examiner

PD response depend on PS bias

Estimated PS efficiency

INTEGRATED PLASMONIC CIRCUIT AND METHOD OF MANUFACTURING THE SAME

CROSS-REFERENCE TO RELATED APPLICATIONS

This application claims priority under 35 U.S.C. §119 to Korean Patent Application No. 10-2016-0005556, filed on Jan. 15, 2016, in the Korean Intellectual Property Office, the disclosure of which is incorporated herein by reference in its entirety.

TECHNICAL FIELD

The following disclosure relates to an integrated plasmonic circuit and a method of manufacturing the same, and more particularly, to a integrated plasmonic circuit including plasmon light emitting and plasmon light receiving devices newly designed using a surface plasmon resonance phenomenon and a link structure between these devices, and a method of manufacturing the same.

BACKGROUND

Surface plasmon indicates collective charge density oscillation generated on a surface of a metal thin film, and a surface plasmon wave generated by the surface plasmon is a surface electromagnetic wave moving along a boundary surface between a metal and a dielectric. This will be described below in more detail. A great number of free electrons are present in the metal, which is a conductor. Since the free electrons are not bound to metal atoms, they may easily respond to an external specific stimulus. A phenomenon that electrons in the material as described above simultaneously oscillate is called plasmon. Particularly, when a size of a surface structure of the metal is a nano level, a surface plasmon resonance phenomenon that the metal has a unique optical property due to behavior of these free electrons appears.

The surface plasmon resonance phenomenon indicates a phenomenon that the free electrons of a surface of the metal collectively oscillate due to resonance with an electromagnetic field of specific energy of light when the light is incident between surfaces of metal nano particles, which are conductors, and a dielectric such as air, water, or the like. That is, in the metal nano particles, an electric field of light in a visible ray to near-infrared ray band and a plasmon are paired with each other, such that light absorption is generated, thereby representing a clear color (in this case, another similar particle generated by coupling the plasmon and a photon to each other is called a surface plasmon polariton). This phenomenon is called a surface plasmon resonance phenomenon, and has an effect that an electromagnetic field is significantly amplified in local regions, which are peripheral portions of metal nano structures. This local surface plasmon resonance phenomenon is induced by conductive nano particles or metal nano structures having a size smaller than a wavelength of incident light, and a frequency of the surface plasmon resonance is changed by sizes or forms of the metal nano particles, a solvent in which the metal nano particles are dispersed, or the like.

One of the typical technologies using the surface plasmon resonance phenomenon as described above is a surface-enhanced Raman spectroscopy (SERS). The surface-enhanced Raman spectroscopy (SERS) is to perform measurement using a phenomenon that Raman-scattering signals, which are unique spectra appearing when light passes through a material, are amplified billions of times on surfaces on which nano structures are formed, by the local surface plasmon resonance as described above. In more detail, when a target material to be detected is coated on a substrate on which the nano structures are formed and light is incident to the substrate, the Raman-scattering signals are generated and amplified by the target material to be detected, and are detected, thereby making it possible to decide the corresponding material. The surface-enhanced Raman spectroscopy as described above has been widely used in various fields such as pharmaceutical field, material science field, drug detection field, and bio-molecule detection field, and the like.

Meanwhile, in the case of a general semiconductor based electronic device circuit, which has a size of tens of nanometers or less, a degree of integration of the circuit is high, while it is difficult for a frequency speed of a signal to exceed 10 GHz. Therefore, research into an optical device as an alternative to the electronic device has been actively conducted. The optical device has a large advantage that a high speed of 100 GHz may be obtained, but also has a diffraction limitation of light, such that it is difficult to reduce a size of a basic device to about hundreds of nanometers or less. As a result, it is difficult to increase a degree of integration of a circuit. That is, an existing dielectric based optical device may not confine light in a region smaller than a wavelength, such that it may not be manufactured at a size as small as the electronic device.

However, as described above, at the time of the surface plasmon resonance, an effect that the electromagnetic field is significantly amplified in the local regions, which are the peripheral portions of the metal nano particles, appears, which means that light energy is converted on a surface plasmon to thereby be accumulated on surfaces of the metal nano particles. This also means that light may be controlled in a region smaller than the diffraction limitation of the light. Therefore, research into an optical device using the plasmon resonance has been variously conducted actively.

An example of a technology developed depending on this research includes Korean Patent Laid-Open Publication No. 10-2015-0138890 (entitled "Method of Preparing Surface Plasmon Resonance-based Light Emitting Diode Using Insulator Film and published on Dec. 11, 2015) (hereinafter, referred to as Related Art Document 1), Korean Patent No. 1559194 (entitled "Surface Plasmon Resonance Optical Materials Using Conductive Oxide Nanoparticles, Method for Fabricating the Same and Optical Devices Comprising the Same" and registered on Oct. 2, 2015) (hereinafter, referred to as Related Art Document 2), and the like. In Related Art Document 1, a light emitting diode (LED) device configured to include a first semiconductor layer, a second semiconductor layer, an active layer interposed between the first semiconductor layer and the second semiconductor layer, hole patterns repeatedly formed periodically in the second semiconductor layer, metal regions positioned in the hole patterns, insulator films formed between the hole patterns and the metal regions has been disclosed. The light emitting diode according to Related Art Document 1 is configured to improve light emitting efficiency by generating a plasmon resonance phenomenon between the active layer of the LED structure and the metal regions enclosed by protection films. In Related Art Document 2, an optical material configured to include a medium including a dielectric or a semiconductor and conductive oxide nano particles buried in the medium and interacting with light in a visible ray to ultraviolet ray region to generate surface plasmon resonance has been disclosed.

It may be appreciated from these Related Art Documents that an existing optical device using the surface plasmon resonance is not appropriate for being used to transfer signals and is limited to only a simple light emitting device. As described above, the optical device that is to be used as the alternate to the electronic device should be able to transfer the signals. That is, the optical device should have a light emitting structure, a light receiving structure, and a link structure between the light emitting structure and the light receiving structure. However, in the case of Related Art Documents, these functions may not be realized.

Therefore, a demand for a configuration of an optical device that may ultimately substitute for the electronic device or may be combined with the electronic device by having the light emitting structure, the light receiving structure, and the link structure between the light emitting structure and the light receiving structure has gradually increased.

RELATED ART DOCUMENT

Patent Document

1. Korean Patent Laid-Open Publication No. 10-2015-0138890 (entitled "Method of Preparing Surface Plasmon Resonance-based Light Emitting Diode Using Insulator Film and published on Dec. 11, 2015)
2. Korean Patent No. 1559194 (entitled "Surface Plasmon Resonance Optical Materials Using Conductive Oxide Nanoparticles, Method for Fabricating the Same and Optical Devices Comprising the Same" and registered on Oct. 2, 2015)

SUMMARY

An embodiment of the present invention is directed to providing a integrated plasmonic circuit including a plasmonic source using a surface plasmon resonance phenomenon, a plasmonic detector detecting an optical signal generated in the plasmonic source, and a link structure between the plasmonic source and the plasmonic detector, that is, a signal transferring part, and a method of manufacturing the same. Another embodiment of the present invention is directed to providing a integrated plasmonic circuit capable of realizing both of miniaturization and speed improvement by overcoming both of a limitation of an electronic device in terms of a signal speed in spite of being excellent in terms of miniaturization efficiency and a limitation of an existing optical device in terms of miniaturization due to a diffraction limitation of light in spite of being improved in terms of a signal speed, and a method of manufacturing the same.

In one general aspect, a integrated plasmonic circuit includes: a lower electrode layer 120 extended in a length direction and made of a metal; at least one pair of semiconductor parts 130 disposed on an upper surface of the lower electrode layer 120 and disposed to be spaced apart from each other in the length direction; an upper electrode layer 140 disposed above the lower electrode layer 120 so as to be spaced apart from the lower electrode layer 120 in a vertical direction, having a lower surface contacting the semiconductor parts 130, having a spacing part 145 formed at a position between the semiconductor parts 130 to thereby be separated into at least one pair, and made of a metal; and a dielectric layer 150 interposed in a space between the lower electrode layer 120 and the upper electrode layer 140 and configured to accommodate the semiconductor parts 130 therein, wherein a plasmonic signal generated in one of one pair of semiconductor parts 130 is guided through the dielectric layer 150 and is transferred to the other semiconductor part 130.

The semiconductor parts 130 may have a form in which an N-type semiconductor and a P-type semiconductor are sequentially stacked in the vertical direction, the lower electrode layer 120 may be grounded, a negative polarity may be applied to the upper electrode layer 140 linked to one of one pair of semiconductor parts 130, and a positive polarity may be applied to the upper electrode layer 140 linked to the other semiconductor part 130. Therefore, the semiconductor part 130 to which the negative polarity is applied may form a plasmonic source (PS), the semiconductor part 130 to which the positive polarity is applied may form a plasmonic detector (PD), and a laminate of the upper electrode layer 140, the dielectric layer 150, and the lower electrode layer 120 between the plasmonic source (PS) and the plasmonic detector (PD) may form a metal-insulator-metal waveguide (MIM WG).

Alternatively, in the integrated plasmonic circuit 100, disposition of an N-type semiconductor and a P-type semiconductor and directions of polarities may be opposite to those of the above exemplary embodiment. That is, in this case, the semiconductor parts 130 may have a form in which a P-type semiconductor and an N-type semiconductor are sequentially stacked in the vertical direction, the lower electrode layer 120 may be grounded, a positive polarity may be applied to the upper electrode layer 140 linked to one of one pair of semiconductor parts 130, and a negative polarity may be applied to the upper electrode layer 140 linked to the other semiconductor part 130. Therefore, the semiconductor part 130 to which the positive polarity is applied may form a plasmonic source (PS), the semiconductor part 130 to which the negative polarity is applied may form a plasmonic detector (PD), and a laminate of the upper electrode layer 140, the dielectric layer 150, and the lower electrode layer 120 between the plasmonic source (PS) and the plasmonic detector (PD) may form a metal-insulator-metal waveguide (MIM WG).

A surface plasmon resonance phenomenon may be generated on surfaces of the lower electrode layer 120 and the upper electrode layer 140 by light generated in the plasmonic source (PS), such that polaritons are excited, and the plasmonic signal generated by the excitation of the polaritons may be transmitted, the plasmonic signal may be transferred through the metal-insulator-metal waveguide (MIM WG), and the plasmonic signal may be received in the plasmonic detector (PD) and be converted into an electrical signal, such that communication of the plasmonic signal from the plasmonic source (PS) to the plasmonic detector (PD) through the metal-insulator-metal waveguide (MIM WG) is performed.

In order to prevent light generated in the plasmonic source (PS) and the plasmonic signal generated by the light from being mixed with each other and being transferred to the plasmonic detector (PD), a thickness d of the dielectric layer 150 configuring the metal-insulator-metal waveguide (MIM WG) may be a cut-off thickness or less at which only a signal having a single plasmonic mode passes.

In order to reduce the thickness d of the dielectric layer 150 configuring the metal-insulator-metal waveguide (MIM WG) to the cut-off thickness or less, depression parts 125 may be formed in regions of the lower electrode layer 120 provided with the semiconductor parts 130.

The integrated plasmonic circuit 100 may further include a substrate 110 provided on a lower surface of the lower electrode layer 120.

The lower electrode layer 120 and the upper electrode layer 140 may be made of the same metal or different metals.

In another general aspect, a method of manufacturing the integrated plasmonic circuit as described above includes: a semiconductor layer forming step of forming a semiconductor layer on an upper surface of a base layer by epitaxy; a semiconductor part forming step of forming at least one pair of semiconductor parts 130 by disposing at least one pair of masks on partial regions of an upper surface of the semiconductor layer and removing the semiconductor layer in regions except for the masks; a dielectric layer forming step of forming the dielectric layer 150 having a form in which the semiconductor parts 130 are accommodated in a dielectric by supplying the dielectric onto the upper surface of the base layer; a lower electrode layer forming step of forming the lower electrode layer 120 by depositing a metal on an upper surface of the dielectric layer 150; a base layer removing step of overturning a laminate including the base layer, the semiconductor parts 130, the dielectric layer 150, and the lower electrode layer 120 and removing the base layer; and an upper electrode layer forming step of forming the upper electrode layer 140 in which the spacing part 145 is formed by depositing a metal on upper surfaces of the semiconductor parts 130 and the dielectric layer 150 and removing the metal in a partial region between the semiconductor parts 130.

In the dielectric layer forming step, the dielectric may be supplied so that an upper surface of the semiconductor part 130 and an upper surface of the dielectric are planarized. Alternatively, in the dielectric layer forming step, the dielectric may be supplied so that an upper surface of the semiconductor part 130 protrudes from an upper surface of the dielectric, such that a portion of the semiconductor part 130 may be inserted into the lower electrode layer 120.

In the base layer removing step, the laminate may be put on the substrate 110, such that the lower electrode layer 120 is disposed on the substrate 110.

In the upper electrode layer forming step, the spacing part 145 may be formed by disposing a mask at a position of the spacing part 145, depositing the metal, and then removing the mask. In the upper electrode layer forming step, the spacing part 145 may be formed by depositing the metal and then removing a portion of the metal by a post-processing process.

DETAILED DESCRIPTION OF MAIN ELEMENTS

Figure 1A:
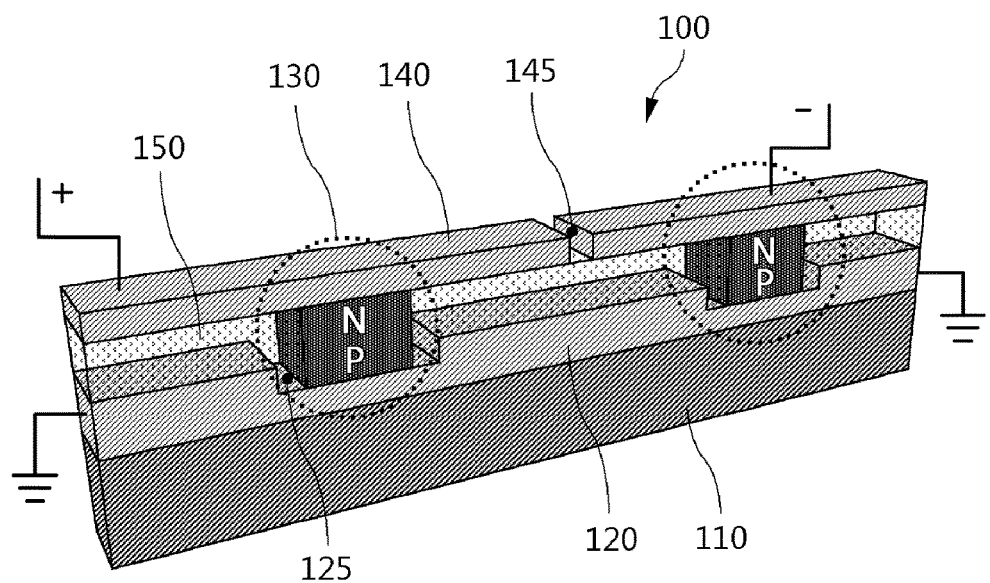
FIGS. 1A and 1B are schematic views of an integrated plasmonic circuit according to an exemplary embodiment of the present invention.

100: integrated plasmonic circuit
110: substrate
120: lower electrode layer
125: depression part
130: semiconductor part
140: upper electrode layer
145: spacing part
150: dielectric layer

DETAILED DESCRIPTION OF EMBODIMENTS

Hereinafter, an integrated plasmonic circuit and a method of manufacturing the same according to an exemplary embodiment of the present invention will be described with reference to the accompanying drawings.

Figure 1B:
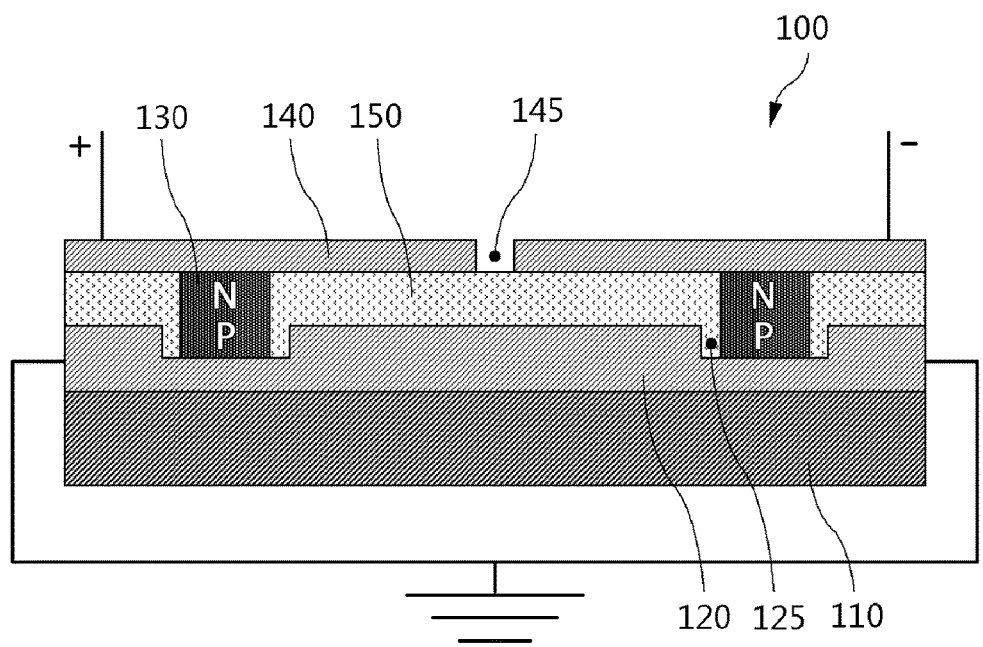
Figure 2:
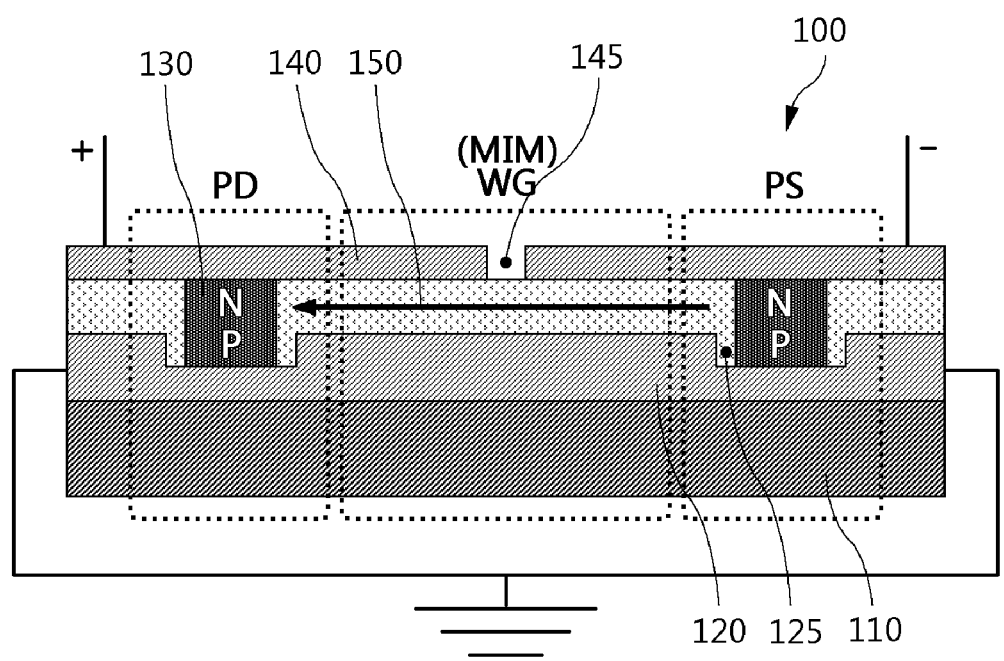
FIG. 2 is a circuit diagram of the integrated plasmonic circuit according to an exemplary embodiment of the present invention.
Figure 2:
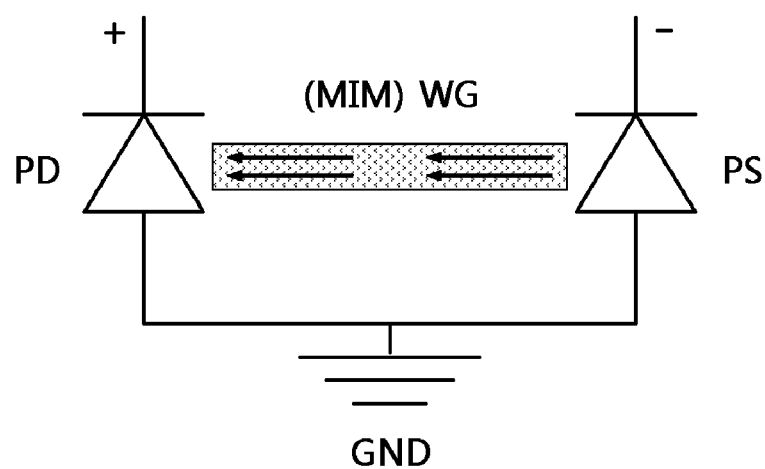
Figure 3:
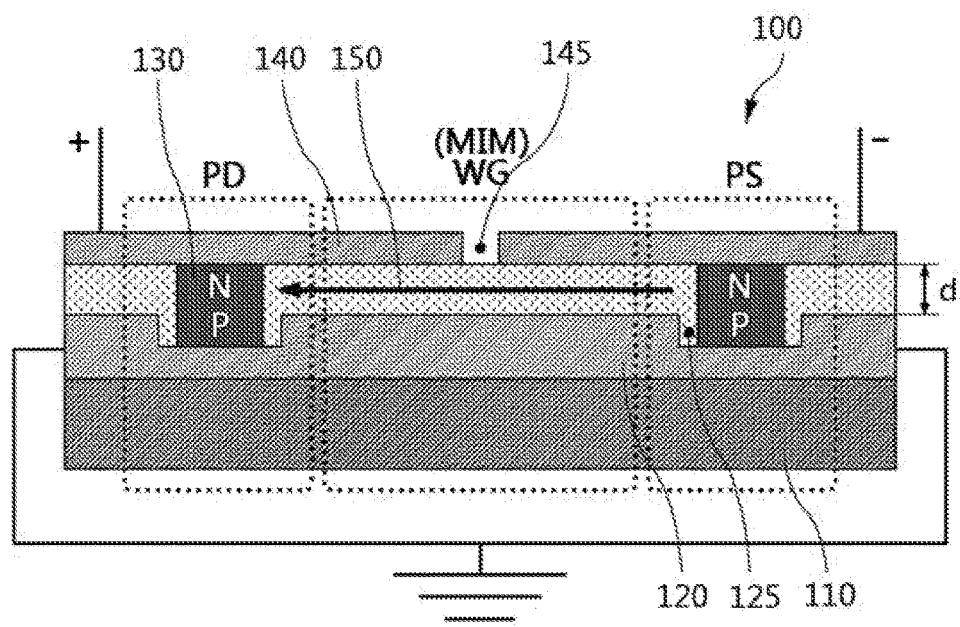
FIG. 3 is a view for describing an operation principle of the integrated plasmonic circuit according to an exemplary embodiment of the present invention.
Figure 3:
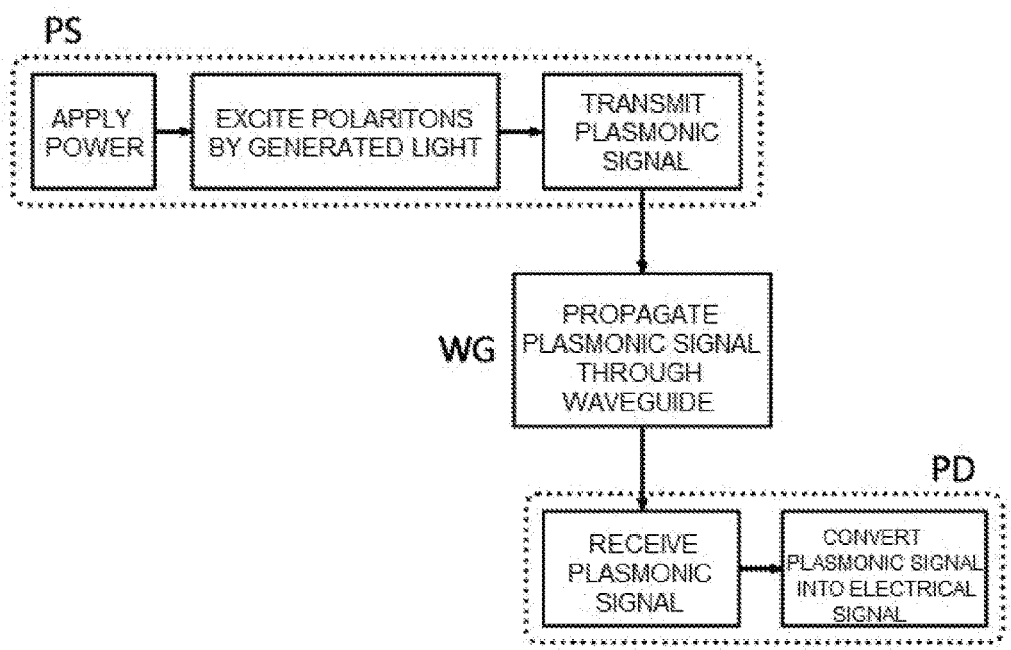

FIGS. 1A and 1B are schematic views a integrated plasmonic circuit according to an exemplary embodiment of the present invention, FIG. 2 is a circuit diagram of the integrated plasmonic circuit according to an exemplary embodiment of the present invention, and FIG. 3 is a view for describing an operation principle of the integrated plasmonic circuit according to an exemplary embodiment of the present invention. As illustrated in FIGS. 1A and 1B, the integrated plasmonic circuit 100 according to an exemplary embodiment of the present invention may be configured to basically include a lower electrode layer 120, semiconductor parts 130, an upper electrode layer 140, and a dielectric layer 150, and be configured to further include a substrate 110 in order to improve structural stability. Meanwhile, throughout the following description, a "vertical direction" is not an absolutely fixed direction, but is a relative direction. For example, a direction in which the lower electrode layer 120 is disposed will be called a lower side and a direction in which the upper electrode layer 140 is disposed will be called an upper side, regardless of whether the integrated plasmonic circuit is disposed in parallel with a ground, is disposed perpendicularly to the ground, is overturned, or the like. Hereinafter, the respective components will be described in more detail.

Since the substrate 110 is not substantially related with a plasmonic signal transfer operation in the integrated plasmonic circuit according to an exemplary embodiment of the present invention to be described in detail below, it may be functionally omitted. However, it is preferable that the substrate 110 is provided when considering convenience of a manufacturing process, structural stability of a completed optical device, or the like. The substrate 110 may be a wafer used as a substrate of a general device, or the like, and be a flexible film form in the case in which it provides flexibility to an optical device.

The lower electrode layer 120 is extended in a length direction, and is made of a metal. The lower electrode layer 120 needs to be made of the metal since it is an electrical conductor in order to apply a voltage thereto. In addition, the lower electrode layer 120 needs to be made of the metal due to the following reason. Although described in more detail below, an object of the present invention is to realize transmission and reception of signals using a surface plasmon resonance phenomenon, which is generated on surfaces of metal nano structures. Therefore, the lower electrode layer 120 needs to be necessarily made of the metal. When considering this point, it is preferable that a metal selected as a material of the lower electrode layer 120 is not selected mainly in consideration of whether or not it has high conductivity, but is selected in consideration of whether or not the surface plasmon resonance phenomenon may be generated well as well as whether or not it has the high conductivity so that a function of the lower electrode layer 120 as an electrode is excellent. The generation of the surface plasmon resonance phenomenon is not related to only the metal, but is variously changed by shape conditions such as sizes, spacing, distribution levels, and the like, of nano structures formed on a surface of the metal, an optical condition such as a wavelength of light incident to the corresponding metal, and the like. Therefore, a material of the lower electrode layer 120 may be appropriately selected in consideration of all of these several conditions.

The semiconductor parts 130 are disposed on an upper surface of the lower electrode layer 120, and at least one pair of semiconductor parts 130 are disposed to be spaced apart from each other in the length direction. Although described in more detail below, as illustrated in FIGS. 1A and 1B, etc., at least one pair of semiconductor parts 130 are paired with each other. Therefore, when a plasmonic signal is transmitted from any one of the semiconductor parts 130, the other of the semiconductor parts 130 receives the plasmonic signal, such that communication is performed. That is, at least one pair of semiconductor parts 130 need to be necessarily provided in order that the "communication" is performed. However, the present invention is not limited thereto, but is variously modified. For example, several pairs of semiconductor parts 130 may be provided, such that communication may be independently performed between the respective pairs of semiconductor parts 130, or signals transmitted from two or more semiconductor parts 130 may be received in one semiconductor part 130.

The upper electrode layer 140 is made of a metal, similar to the lower electrode layer 120, and is disposed above the lower electrode 120 so as to be spaced apart from the lower electrode layer 120 in the vertical direction so that a lower surface thereof contacts the semiconductor parts 130. Here, the upper electrode layer 140 has a spacing part 145 formed at a position between the semiconductor parts 130, such that it is separated into at least one pair. As described above, at least one pair of semiconductor parts 130 are provided for the purpose of transmission and reception, and although described in more detail below, it is determined whether the semiconductor parts 130 are used for the purpose of the transmission or the reception by polarities of voltages applied to the corresponding semiconductor parts 130 or relative voltages. Therefore, the upper electrode layer 140 needs to be separated for each of the semiconductor parts 130 in order to apply different voltages to each of the semiconductor parts 130.

The dielectric layer 150 is interposed in a space between the lower electrode layer 120 and the upper electrode layer 140, and is configured to accommodate the semiconductor parts 130 therein, as illustrated in FIGS. 1A and 1B, etc. The plasmonic signal is transferred through the dielectric layer 150. A material of the dielectric layer 150 may be appropriately determined so as to have a medium refractive index advantageous in transferring the plasmonic signal in consideration of this point.

In the integrated plasmonic circuit according to an exemplary embodiment of the present invention having the configuration as described above, the plasmonic signal generated in one of one pair of semiconductor parts 130 is guided through the dielectric layer 150 and is transferred to the other semiconductor part 130, such that communication is performed.

A configuration and an operation principle of the integrated plasmonic circuit according to an exemplary embodiment of the present invention will be described in more detail with reference to FIGS. 2 and 3.

In the integrated plasmonic circuit according to an exemplary embodiment of the present invention, as an example, the semiconductor parts 130 may have a form in which an N-type semiconductor and a P-type semiconductor are sequentially stacked in the vertical direction. In this case, as a configuration for applying power, the lower electrode layer 120 is grounded, a negative polarity is applied to the upper electrode layer 140 linked to one of one pair of semiconductor parts 130, and a positive polarity is applied to the upper electrode layer 140 linked to the other semiconductor part 130.

A general light emitting diode is configured of a pair of N-type semiconductor and P-type semiconductor, and when the negative polarity is applied to the N-type semiconductor and the positive polarity is applied to the P-type semiconductor, free electrons are generated in the N-type semiconductor simultaneously with generation of light. When considering this point, it may be appreciated that the semiconductor part 130 to which the negative polarity is applied forms a plasmonic source (PS) and the semiconductor part 130 to which the positive polarity is applied naturally forms a plasmonic detector (PD). Here, a laminate of the upper electrode layer 140, the dielectric layer 150, and the lower electrode layer 120 between the plasmonic source (PS) and the plasmonic detector (PD) forms a metal-insulator-metal waveguide (MIM WG) to guide the plasmonic signal.

A detailed description therefor will be provided below. As illustrated in FIG. 3, when power is applied to the plasmonic source (PS), light is generated in the plasmonic source (PS). Here, a surface plasmon resonance phenomenon is generated on surfaces of the lower electrode layer 120 and the upper electrode layer 140 by the light generated in the plasmonic source (PS), such that polaritons are excited. The plasmonic signal generated by the excitation of the polaritons is transmitted, and is naturally transferred through the metal-insulator-metal waveguide (MIM WG).

Here, when the upper electrode layer 140 and the lower electrode layer 120 are not present on and beneath the dielectric layer 150, the plasmonic signal may be diffused to the outside of an optical device. However, the plasmonic signal is blocked by two electrode layers made of the metal, such that it may move through only the dielectric layer 150. That is, since upper and lower portions of the metal-insulator-metal waveguide (MIM WG) are made of a metal, the metal-insulator-metal waveguide (MIM WG) may prevent the plasmonic signal from being leaked to the outside, and since an inner portion of the metal-insulator-metal waveguide (MIM WG) is made of a dielectric, the plasmonic signal may be transferred through the metal-insulator-metal waveguide (MIM WG), such that the metal-insulator-metal waveguide (MIM WG) may very smoothly guide movement of the plasmonic signal.

The plasmonic signal transferred through the metal-insulator-metal waveguide (MIM WG) is received in the plasmonic detector (PD), and is converted into an electrical signal, whereby communication of the plasmonic signal from the plasmonic source (PS) to the plasmonic detector (PD) through the metal-insulator-metal waveguide (MIM WG) may be performed.

In FIGS. 1A and 1B, etc., an example in which the semiconductor parts 130 have the form in which the N-type semiconductor and the P-type semiconductor are sequentially stacked in the vertical direction, the semiconductor part 130 disposed at a side at which the negative polarity is applied to the upper electrode layer 140 forms the plasmonic source (PS), and the semiconductor part 130 disposed at a side at which the positive polarity is applied to the upper electrode layer 140 forms the plasmonic detector (PD), as described above, is illustrated. However, the present invention is not limited to this configuration. That is, the semiconductor parts 130 may also have a form in which the P-type semiconductor and the N-type semiconductor are sequentially stacked in the vertical direction. In this case, polarities of voltages for forming the plasmonic source (PS) and the plasmonic detector (PD) may be exchanged with each other. In detail, the lower electrode layer 120 is grounded, the positive polarity is applied to the upper electrode layer 140 linked to one of one pair of semiconductor parts 130, and the negative polarity is applied to the upper electrode layer 140 linked to the other semiconductor part 130. In this case, the semiconductor part 130 to which the positive polarity is applied forms the plasmonic source (PS), the semiconductor part 130 to which the negative polarity is applied forms the plasmonic detector (PD), and a laminate of the upper electrode layer 140, the dielectric layer 150, and the lower electrode layer 120 between the plasmonic source (PS) and the plasmonic detector (PD) forms the metal-insulator-metal waveguide (MIM WG). Since transmission, propagation, reception principles of the plasmonic signal in this example are the same as those of the plasmonic signal in an example illustrated in FIGS. 1A and 1B, etc., a description therefor will be omitted.

Meanwhile, a thickness of the dielectric layer 150 forming the metal-insulator-metal waveguide (MIM WG) needs to be appropriately limited in order to prevent an unnecessary signal from being mixed with the plasmonic signal in a process of guiding and transferring the plasmonic signal to the metal-insulator-metal waveguide (MIM WG). A detailed description therefor will be provided below.

As described above, when the power is applied to the plasmonic source (PS), light is generated from the semiconductor part 130 within the plasmonic source (PS), and the surface plasmon resonance phenomenon is generated on surfaces of the electrode layers formed of the metal in the vicinity of the semiconductor part 130 by the light. A function that is to be ultimately implemented in the optical device according to an exemplary embodiment of the present invention is to transfer the plasmonic signal generated by the surface plasmon resonance phenomenon. However, here, light also is a kind of electromagnetic wave, such that the light may be sufficiently transferred through the dielectric layer 150. That is, when an optical signal is transferred together with the plasmonic signal generated in the semiconductor part 130, desired signal transfer efficiency is not accomplished, and incorrect communication is performed, such that a desired function as an optical device for transferring a signal is not performed.

That is, in order to prevent light generated in the plasmonic source (PS) and the plasmonic signal generated by the light from being mixed with each other and being transferred to the plasmonic detector (PD), in the integrated plasmonic circuit 100 according to an exemplary embodiment of the present invention, it is preferable that a thickness d of the dielectric layer 150 configuring the metal-insulator-metal waveguide (MIM WG) is a cut-off thickness or less at which only a signal having a single plasmonic mode may pass. In this case, the light generated in the plasmonic source (PS) is not propagated through the dielectric layer 150, and only the plasmonic signal may pass through the metal-insulator-metal waveguide (MIM WG) and be then smoothly transferred to the plasmonic detector (PD).

For reference, in FIGS. 1A and 1B, etc., an example in which depression parts 125 are formed in regions of the lower electrode layer 120 provided with the semiconductor parts 130 is illustrated. Even though the depression parts 125 are not formed, the communication of the plasmonic signal depending on the principle as described above may be realized. As described above, when the thickness d of the dielectric layer 150 configuring the metal-insulator-metal waveguide (MIM WG) is the cut-off thickness or more, a problem that the plasmonic signal and the optical signal are mixed with each other may occur. However, when a thickness of the semiconductor part 130 is increased inevitably in a manufacturing process, the thickness of the dielectric layer 150 may also be increased to exceed the cut-off thickness. In this case, as illustrated in FIGS. 1A and 1B, etc., the depression part 125 is formed in the lower electrode layer 120, such that the thickness of the dielectric layer 150 configuring the metal-insulator-metal waveguide (MIM WG) may be reduced to be the cut-off thickness or less even though the thickness of the semiconductor part 130 becomes the cut-off thickness or more.

Figure 4:
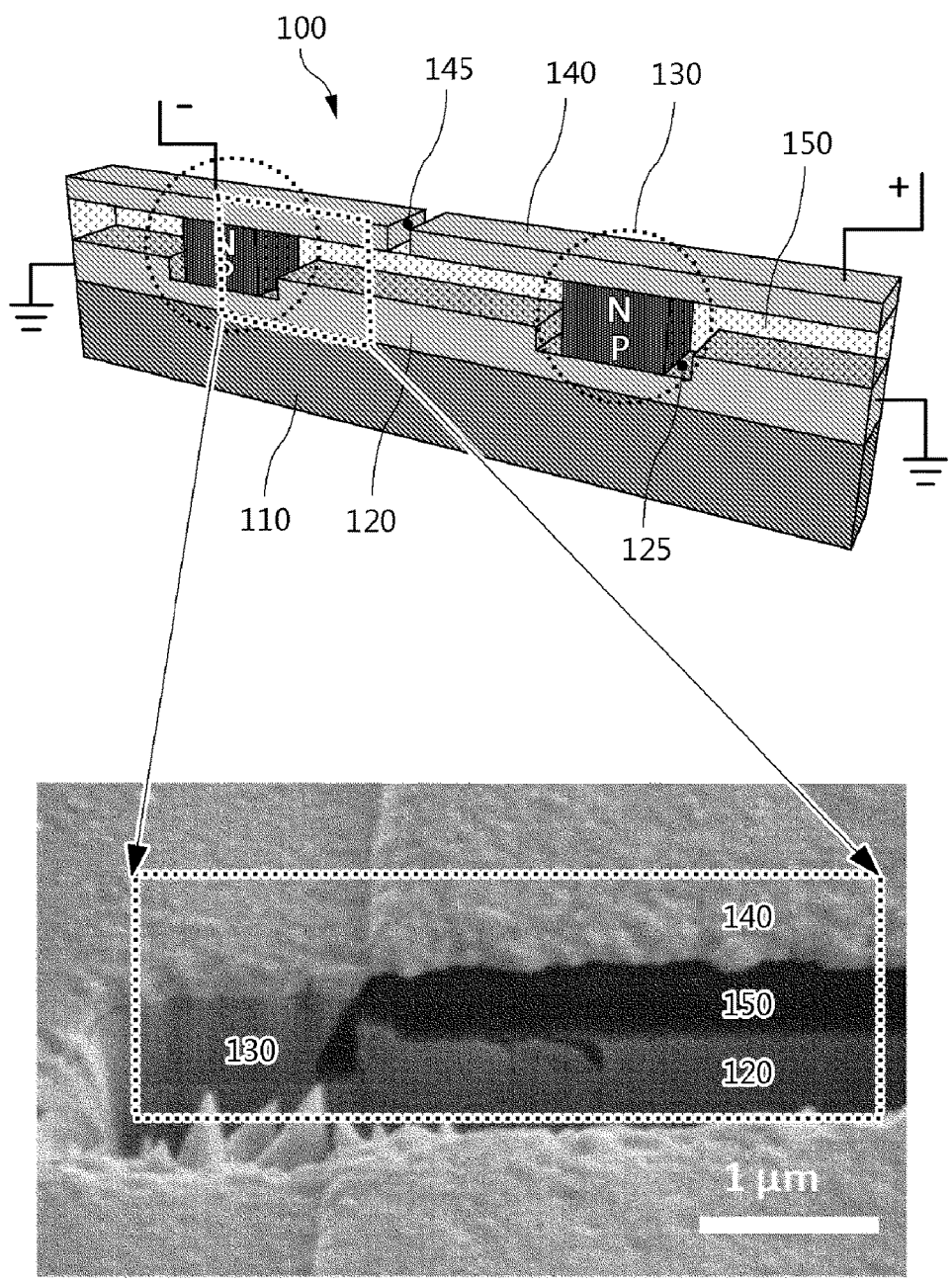
FIG. 4 is a view illustrating a photograph of the integrated plasmonic circuit according to an exemplary embodiment of the present invention.

FIG. 4 is a view illustrating a photograph of the integrated plasmonic circuit according to an exemplary embodiment of the present invention. A lower photograph of FIG. 4, which is a side cross-sectional photograph of an example of the integrated plasmonic circuit actually manufactured based on the concept as described above, captured by a scanning electron microscope (SEM), illustrates portions of the plasmonic source (PS) and the metal-insulator-metal waveguide (MIM WG). Ag was used as materials of the upper electrode layer 140 and the lower electrode layer 120, BCB was used as a material of the dielectric layer 150, and InGaAs was used as a material of the semiconductor part 130. In this case, it was found that it is appropriate that the thickness d of the dielectric layer 150 at which the light generated in the semiconductor part 130 is not propagated to the metal-insulator-metal waveguide (MIM WG) and only the plasmonic signal may be propagated is 500 nm or less. Meanwhile, in the example described above, the lower electrode layer 120 and the upper electrode layer 140 are made of the same metal, which is convenient in analyzing several phenomena related to generation of the plasmonic signal. However, materials of the electrode layers, the dielectric layer, and the semiconductor part are not limited to those of the example described above, but may be variously modified. In addition, since the thickness d is variously modified depending on the materials of the electrode layers and the dielectric layer, a wavelength range of the light generated in the semiconductor part, or the like, the present invention is not limited to the example described above.

Figure 5:
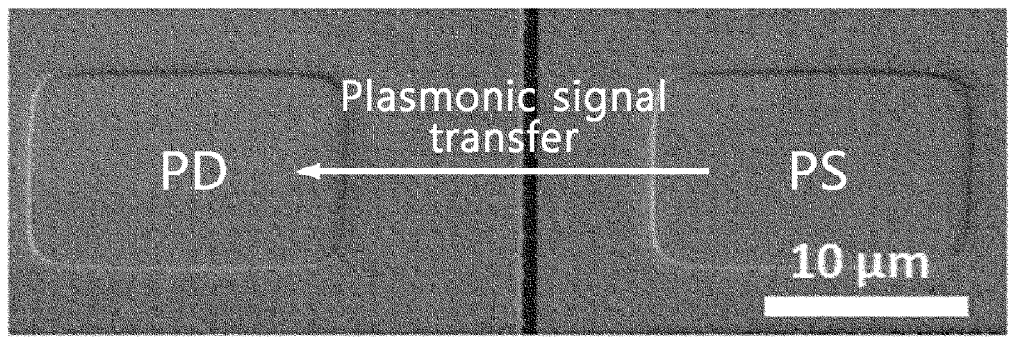
FIG. 5 is a view illustrating a photograph and an experiment result of the integrated plasmonic circuit according to an exemplary embodiment of the present invention.
Figure 5:
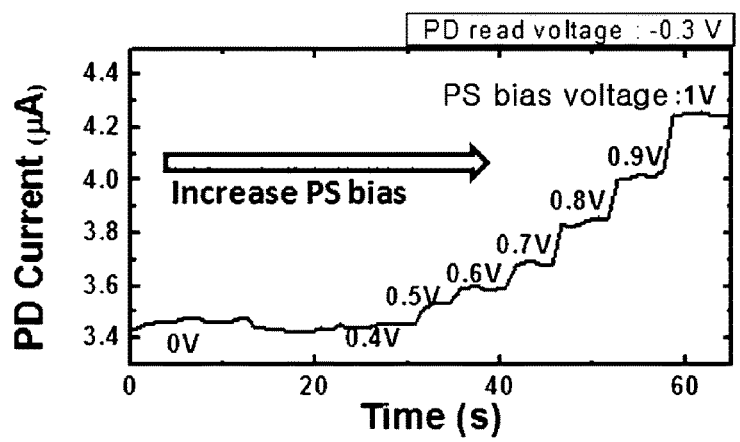
Figure 5:
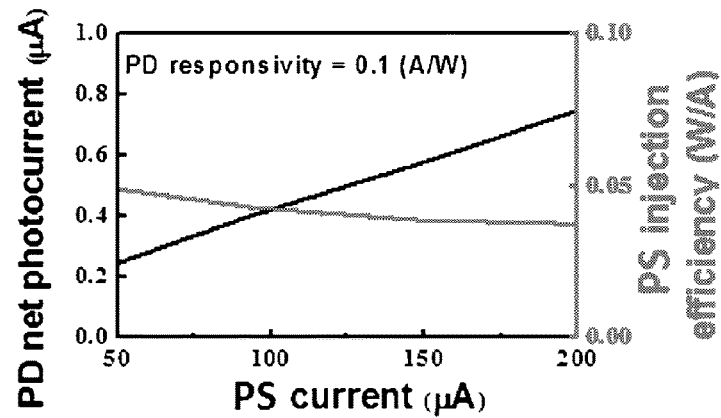

FIG. 5 is a view illustrating a photograph and an experiment result of the integrated plasmonic circuit according to an exemplary embodiment of the present invention. An upper view of FIG. 5 is a photograph of the integrated plasmonic circuit viewed from the top, and an intermediate view and a lower view of FIG. 5 are graphs illustrating experimental results for whether or not a signal is smoothly transferred from the plasmonic source (PS) to the plasmonic detector (PD). Referring to the graph of the intermediate view, it may be confirmed that the larger the bias voltage in the plasmonic source (PS), the larger the current value in the plasmonic detector (PD). In addition, referring to the graph of the lower view, it may be confirmed that a relationship between a plasmonic source (PS) injection efficiency value depending on a value of a current flowing in the plasmonic source (PS) and a value of a PD net photocurrent detected in the power detector (PD) clearly appears. That is, it may be appreciated from FIG. 5 that the value of the PD net photocurrent detected in the power detector (PD) is related to a value of a voltage applied in the plasmonic source (PS), and it may be ultimately confirmed that the communication from the plasmonic source (PS) to the plasmonic detector (PD) is smoothly performed.

As described above, in the case of the existing electronic device used in the integrated circuit, which has a size of tens of nanometers or less, a degree of integration of the circuit is high, while it is difficult for a frequency speed of a signal to exceed 10 GHz. In addition, the existing dielectric based optical device has a large advantage that a high speed of 100 GHz may be obtained, but also it may not confine light in a region smaller than a wavelength due to a diffraction limitation of light, such that it is difficult to reduce a size of a basic device to about hundreds of nanometers or less. As a result, it is difficult to increase a degree of integration of a circuit.

However, according to an exemplary embodiment of the present invention, since the plasmonic signal generated by the surface plasmon resonance phenomenon is used for communication, as described above, light may be controlled in a region smaller than the diffraction limitation of the light, such that a size of the optical device may be significantly reduced as compared with the existing device. Further, since the light is substantially used for the communication, a rapid communication speed, which is an advantage of the optical device as described above, may be secured. That is, the integrated plasmonic circuit according to an exemplary embodiment of the present invention may be miniaturized, such that a degree of integration may be increased as compared with the existing optical device, and an advantage of the optical device, that is, a speed more rapid than that of the existing electronic device may be secured.

Figure 6A:
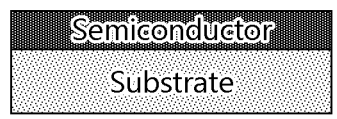
FIGS. 6A, 6B, 6C, 6D, 6E, and 6F are schematic views of a method of manufacturing an integrated plasmonic circuit according to an exemplary embodiment of the present invention.
Figure 6B:
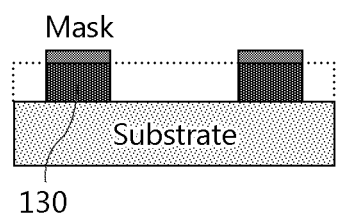
Figure 6C:
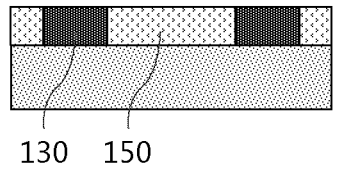
Figure 6D:
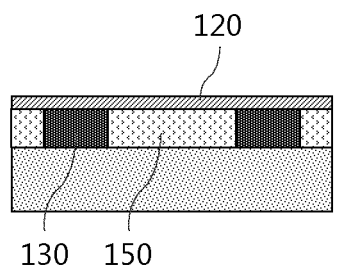
Figure 6E:
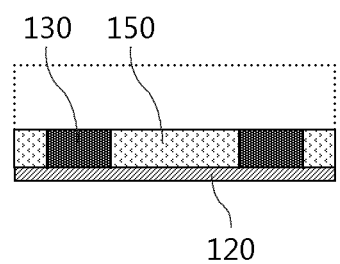
Figure 6F:
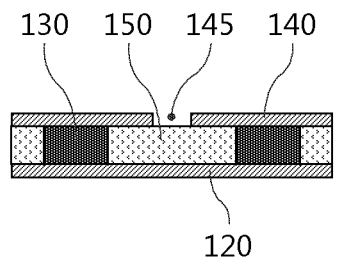
Figure 7:
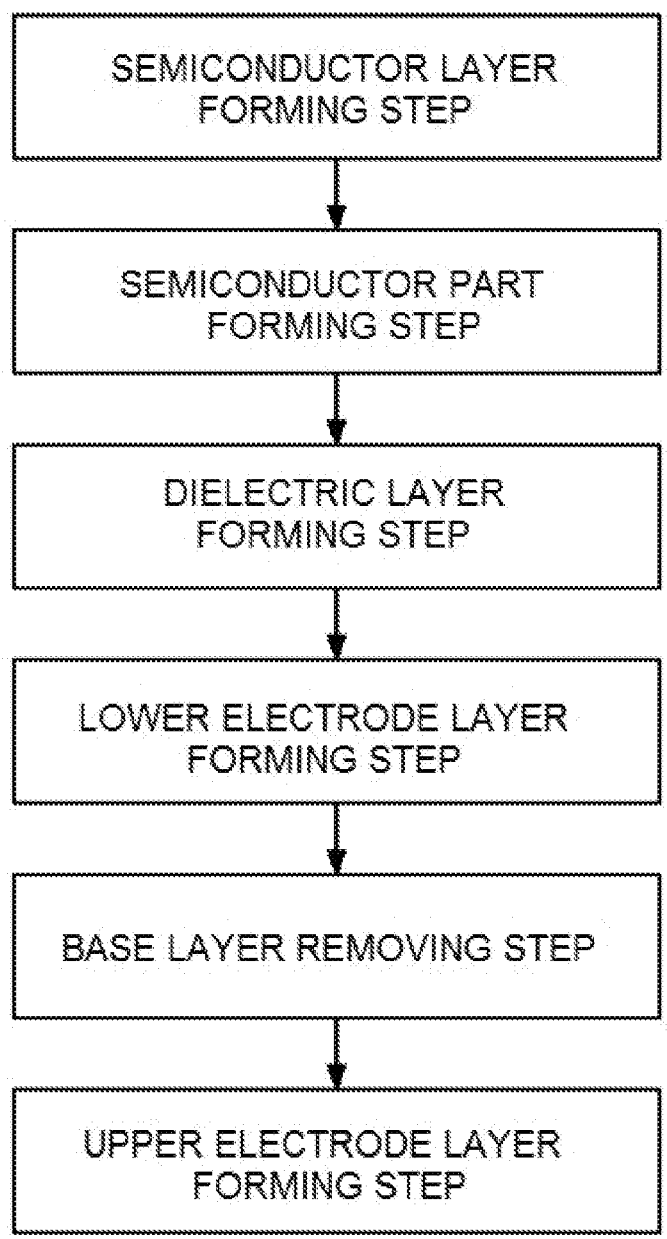
FIG. 7 is a flow chart of the method of manufacturing an integrated plasmonic circuit according to an exemplary embodiment of the present invention.

FIGS. 6A to 6F are schematic views of a method of manufacturing a integrated plasmonic circuit according to an exemplary embodiment of the present invention, and FIG. 7 is a flow chart of the method of manufacturing a integrated plasmonic circuit according to an exemplary embodiment of the present invention.

As illustrated in FIGS. 6A to 6F, etc., first, in a semiconductor layer forming step, semiconductor layers are formed on an upper surface of a base layer by epitaxy, as illustrated in FIG. 6A. The epitaxy, which indicates a phenomenon that any crystal is grown on a surface of another crystal while having a specific orientation relationship, is an actually widely used method. For example, the epitaxy is used to form a crystal thin film by a deposition method.

Next, in a semiconductor part forming step, as illustrated in FIG. 6B, at least one pair of masks are disposed on partial regions of an upper surface of the semiconductor layer, and the semiconductor layer is removed in regions except for the masks, such that at least one pair of semiconductor parts 130 are formed. As described above, at least one pair of semiconductor parts 130 or at least one pair or more of semiconductor parts 130 may be provided, and the masks may also be disposed so that the number and positions thereof correspond to those of semiconductor parts 130. In addition, the masks may be removed after the semiconductor parts 130 are formed or may be left so as to be removed in another step later. This may be appropriately determined depending on a material of the mask, a desired structure of the optical device of which manufacturing is completed later, or the like.

Next, in a dielectric layer forming step, as illustrated in FIG. 6C, a dielectric is supplied onto the upper surface of the base layer, such that the dielectric layer 150 having a form in which the semiconductor parts 130 are accommodated in the dielectric is formed. Here, in FIG. 6C, in the dielectric layer forming step, an example in which the dielectric is supplied so that an upper surface of the semiconductor part 130 and an upper surface of the dielectric are planarized is illustrated. In this case, a thickness of the semiconductor part 130 and a thickness of the dielectric layer 150 become equal to each other. However, a case in which the semiconductor part 130 is formed at a thickness thicker than the cut-off thickness (described above) inevitably in a manufacturing process may occur. In this case, in order to reduce the thickness of the dielectric layer 150 configuring the metal-insulator-metal waveguide (MIM WG), in the dielectric layer forming step, the dielectric is supplied so that the upper surface of the semiconductor part 130 protrudes from the upper surface of the dielectric, thereby making it possible to allow a portion of the semiconductor part 130 to be inserted into the lower electrode layer 120. In this case, the depression parts 125 may be naturally formed at positions of the lower electrode layer 120 corresponding to the semiconductor parts 130.

Next, in a lower electrode layer forming step, as illustrated in FIG. 6D, a metal is deposited on an upper surface of the dielectric layer 150, such that the lower electrode layer 120 is formed. As described above, in the case in which the planarization is performed in the dielectric layer forming step, only the deposition of the metal is simply performed in the lower electrode layer forming step. However, in the case in which the lower electrode layer forming step is performed in a state in which the semiconductor part 130 protrudes in the dielectric layer forming step, a process change such as an increase in a deposition time for accomplishing the planarization may be required in this point in time.

Next, in a base layer removing step, as illustrated in FIG. 6E, a laminate including the base layer, the semiconductor parts 130, the dielectric layer 150, and the lower electrode layer 120 is overturned, and the base layer is removed. In this step, the laminate is put on the substrate 110, such that the lower electrode layer 120 may be disposed on the substrate 110.

Finally, in an upper electrode layer forming step, as illustrated in FIG. 6F, a metal is deposited on the upper surfaces of the semiconductor parts 130 and the dielectric layer 150, and is removed in a partial region between the semiconductor parts 130, such that the upper electrode layer 140 in which the spacing part 145 is formed is formed. Here, the spacing part 145 may be formed by disposing a mask at a position of the spacing part 145, depositing the metal, and then removing the mask. Alternatively, in the upper electrode layer forming step, the spacing part 145 may also be formed by depositing the metal and then removing a portion of the metal by a post-processing process such as a laser irradiating process, or the like.

Through the steps as described above, the integrated plasmonic circuit according to an exemplary embodiment of the present invention as described above may be manufactured.

According to an exemplary embodiment of the present invention, the integrated plasmonic circuit including the plasmonic source using the surface plasmon resonance phenomenon, the plasmonic detector detecting the optical signal generated in the plasmonic source, and a link structure between the plasmonic source and the plasmonic detector, that is, a signal transferring part is suggested, thereby making it possible to realize a signal transfer function while using the surface plasmon resonance phenomenon. In more detail, existing optical devices have performed only a simple light emitting function using the surface plasmon resonance phenomenon. Therefore, it was difficult to realize a signal transfer function necessarily required in a general integrated circuit according to the related art. Therefore, generally, there was a limitation that the electronic device configuring the integrated circuit according to the related art may not be completely replaced by the optical device. However, according to an exemplary embodiment of the present invention, since the signal transfer function may be realized in spite of a form of the optical device, the optical device may easily substitute for the existing electronic device or may be easily combined with the electronic device.

The present invention may further obtain the following effects due to the effect described above. The existing electronic device may be manufactured at a small size of tens of nanometers, has a limitation that it is difficult for a speed of a signal to exceed 10 GHz, and the existing dielectric based optical device has a high speed of a signal of 100 GHz, but it is difficult to miniaturize the existing dielectric based optical device at a size of hundreds of nanometers or less due to the diffraction limitation of the light. However, since the optical device according to an exemplary embodiment of the present invention uses the surface plasmon resonance phenomenon, as described above, the light may be controlled in the region smaller than the diffraction limitation of the light, such that the limitation of the existing dielectric based optical device in terms of the miniaturization may be overcome. In addition, since the optical device according to an exemplary embodiment of the present invention is configured to the plasmonic source, the plasmonic detector, and the signal transferring part to enable the communication, as described above, the electronic device that was used in the existing integrated circuit may be easily replaced by the optical device according to an exemplary embodiment of the present invention or the electronic device and the optical device according to an exemplary embodiment of the present invention may be easily combined with each other.

As described above, according to an exemplary embodiment of the present invention, the existing electronic device may be replaced by or be combined with the optical device, such that both of the miniaturization of the integrated circuit and the speed improvement may be realized.

The present invention is not limited to the above-mentioned exemplary embodiments but may be variously applied, and may be variously modified by those skilled in the art to which the present invention pertains without departing from the gist of the present invention claimed in the claims.

What is claimed is:

1. An integrated plasmonic circuit comprising:
a lower electrode layer extended in a length direction and made of a metal;
at least one pair of semiconductor parts disposed on an upper surface of the lower electrode layer and disposed to be spaced apart from each other in the length direction;
an upper electrode layer disposed above the lower electrode layer so as to be spaced apart from the lower electrode layer in a vertical direction, having a lower surface contacting the semiconductor parts, having a spacing part formed at a position between the semiconductor parts to thereby be separated into at least one pair, and made of a metal; and
a dielectric layer interposed in a space between the lower electrode layer and the upper electrode layer and configured to accommodate the semiconductor parts therein,
wherein a plasmonic signal generated in one of one pair of semiconductor parts is guided through the dielectric layer and is transferred to the other semiconductor part.

2. The integrated plasmonic circuit of claim 1, wherein the semiconductor parts have a form in which an N-type semiconductor and a P-type semiconductor are sequentially stacked in the vertical direction, the lower electrode layer is grounded, a negative polarity is applied to the upper electrode layer linked to one of one pair of semiconductor parts, and a positive polarity is applied to the upper electrode layer linked to the other semiconductor part, such that the semiconductor part to which the negative polarity is applied forms a plasmonic source (PS), the semiconductor part to which the positive polarity is applied forms a plasmonic detector (PD), and a laminate of the upper electrode layer, the dielectric layer, and the lower electrode layer between the plasmonic source (PS) and the plasmonic detector (PD) forms a metal-insulator-metal waveguide (MIM WG), or the semiconductor parts have a form in which a P-type semiconductor and an N-type semiconductor are sequentially stacked in the vertical direction, the lower electrode layer is grounded, a positive polarity is applied to the upper electrode layer linked to one of one pair of semiconductor parts, and a negative polarity is applied to the upper electrode layer linked to the other semiconductor part, such that the semiconductor part to which the positive polarity is applied forms a plasmonic source (PS), the semiconductor part to which the negative polarity is applied forms a plasmonic detector (PD), and a laminate of the upper electrode layer, the dielectric layer, and the lower electrode layer between the plasmonic source (PS) and the plasmonic detector (PD) forms a metal-insulator-metal waveguide (MIM WG).

3. The integrated plasmonic circuit of claim 2, wherein a surface plasmon resonance phenomenon is generated on surfaces of the lower electrode layer and the upper electrode layer by light generated in the plasmonic source (PS), such that polaritons are excited, and the plasmonic signal generated by the excitation of the polaritons is transmitted,
the plasmonic signal is transferred through the metal-insulator-metal waveguide (MIM WG), and
the plasmonic signal is received in the plasmonic detector (PD) and is converted into an electrical signal, such that communication of the plasmonic signal from the plasmonic source (PS) to the plasmonic detector (PD) through the metal-insulator-metal waveguide (MIM WG) is performed.

4. The integrated plasmonic circuit of claim 2, wherein in order to prevent light generated in the plasmonic source (PS) and the plasmonic signal generated by the light from being mixed with each other and being transferred to the plasmonic detector (PD), a thickness of the dielectric layer configuring the metal-insulator-metal waveguide (MIM WG) is a cut-off thickness or less at which only a signal having a single plasmonic mode passes.

5. The integrated plasmonic circuit of claim 4, wherein in order to reduce the thickness of the dielectric layer configuring the metal-insulator-metal waveguide (MIM WG) to the cut-off thickness or less, depression parts are formed in regions of the lower electrode layer provided with the semiconductor parts.

6. The integrated plasmonic circuit of claim 1, further comprising a substrate provided on a lower surface of the lower electrode layer.

7. The integrated plasmonic circuit of claim 1, wherein the lower electrode layer and the upper electrode layer are made of the same metal or different metals.

* * * * *